United States Patent [19]

Kee

[11] Patent Number: 5,582,161
[45] Date of Patent: Dec. 10, 1996

[54] SHEATHED CATHETER ADAPTER AND METHOD OF USE

[75] Inventor: Kok-Hiong Kee, St. Louis, Mo.

[73] Assignee: Sherwood Medical Company, St. Louis, Mo.

[21] Appl. No.: 352,328

[22] Filed: Dec. 8, 1994

[51] Int. Cl.$^6$ ............................................. A61M 16/00
[52] U.S. Cl. .................... 128/200.26; 128/207.14; 128/207.15; 128/912
[58] Field of Search .............. 128/207.14, 207.15, 128/207.16, 912, DIG. 26

[56] References Cited

U.S. PATENT DOCUMENTS

| | | | |
|---|---|---|---|
| 4,240,417 | 12/1980 | Holever | 128/203.12 |
| 4,351,328 | 9/1982 | Bodai | 128/202.16 |
| 4,638,539 | 1/1987 | Palmer | 29/157 R |
| 4,781,702 | 11/1988 | Herrli | 128/912 |
| 4,805,611 | 2/1989 | Hodgkins | 128/207.14 |
| 4,827,921 | 5/1989 | Rugheimer | 128/912 |
| 4,838,255 | 6/1989 | Lambert | 128/202.16 |
| 4,846,167 | 7/1989 | Tibbals | 128/202.27 |
| 4,951,661 | 8/1990 | Sladek | 128/202.27 |
| 5,083,561 | 1/1992 | Russo | 128/207.16 |
| 5,088,486 | 2/1992 | Jinotti | 128/207.14 |
| 5,140,983 | 8/1992 | Jinotti | 128/207.14 |
| 5,158,569 | 10/1992 | Strickland et al. | 604/283 |
| 5,195,994 | 5/1993 | Dieringer | 128/912 |
| 5,215,522 | 6/1993 | Page et al. | 604/33 |
| 5,234,411 | 8/1993 | Vaillancourt | 604/171 |
| 5,254,098 | 10/1993 | Ulrich et al. | 604/171 |
| 5,255,676 | 10/1993 | Russo | 128/207.14 |
| 5,333,607 | 8/1994 | Kee et al. | 128/207.16 |
| 5,343,857 | 9/1994 | Schneider et al. | 128/912 |
| 5,377,672 | 1/1995 | Kee | 128/207.16 |
| 5,404,873 | 4/1995 | Leagre et al. | 128/DIG. 26 |

*Primary Examiner*—Aaron J. Lewis
*Attorney, Agent, or Firm*—Montgomery W. Smith; Ari M. Bai

[57] ABSTRACT

The present invention is directed to a reliable, contamination free, distal end adapter for a suction catheter. The adapter allows the patient to breathe directly therethrough when it is connected to the patient's endotracheal tube for use, and provides an enclosure for preventing exposure of medical personnel to contaminants when withdrawing the catheter from the patient and disconnecting the catheter adapter from the endotracheal tube for disposal.

16 Claims, 5 Drawing Sheets

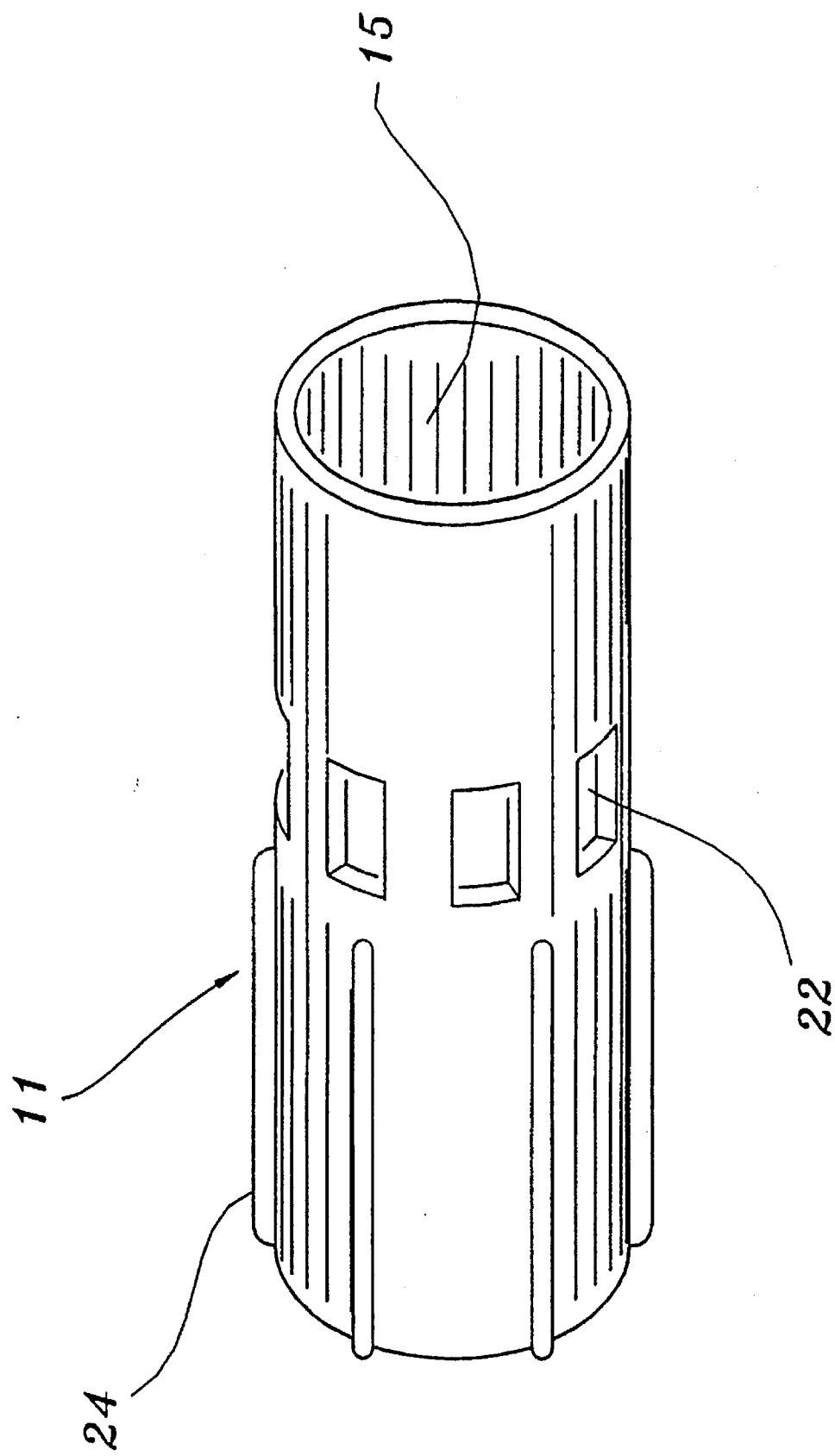

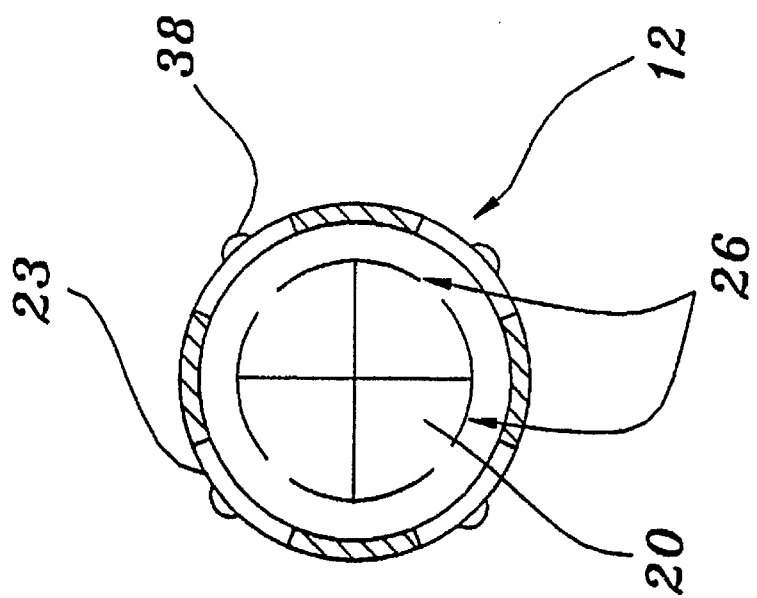
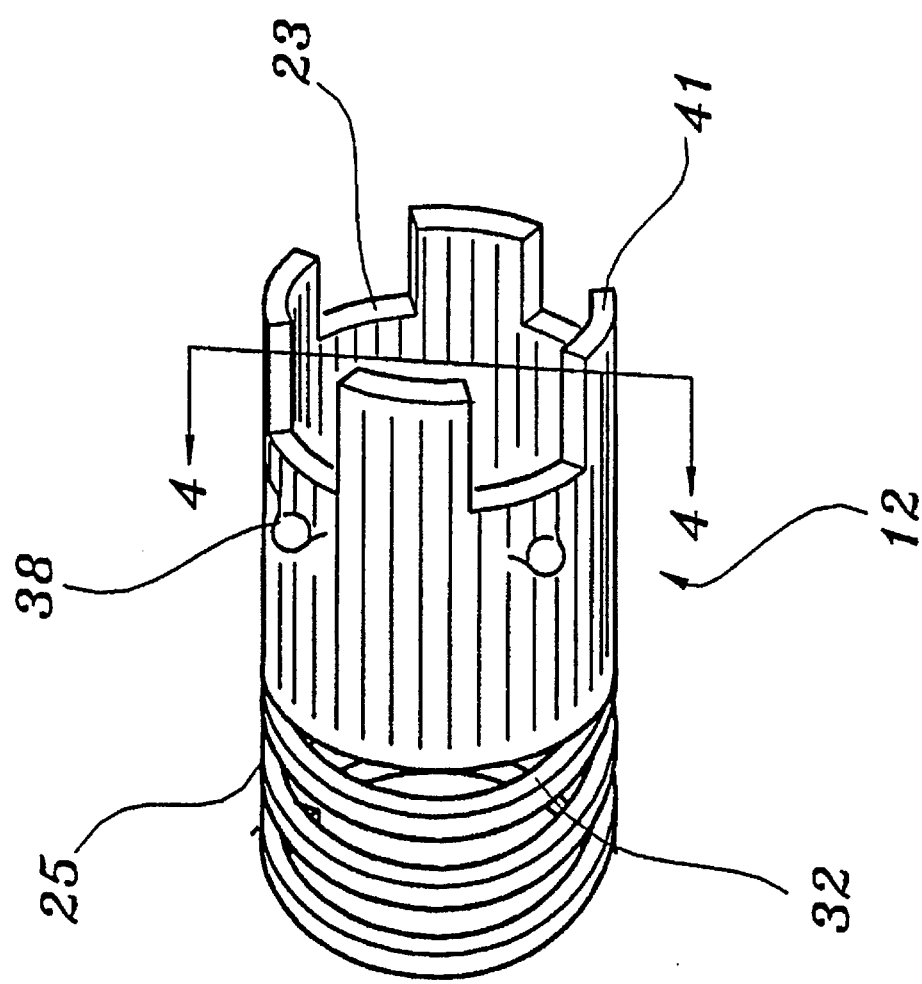

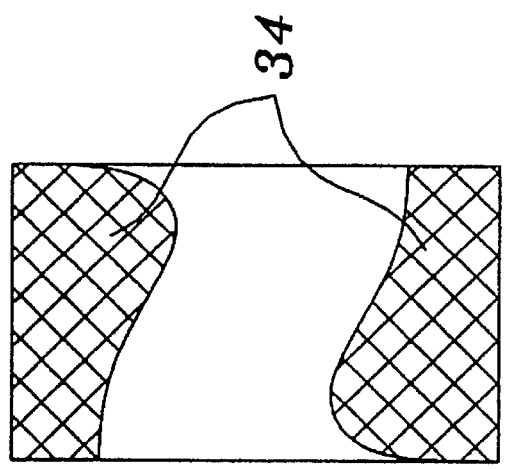
Fig. 8
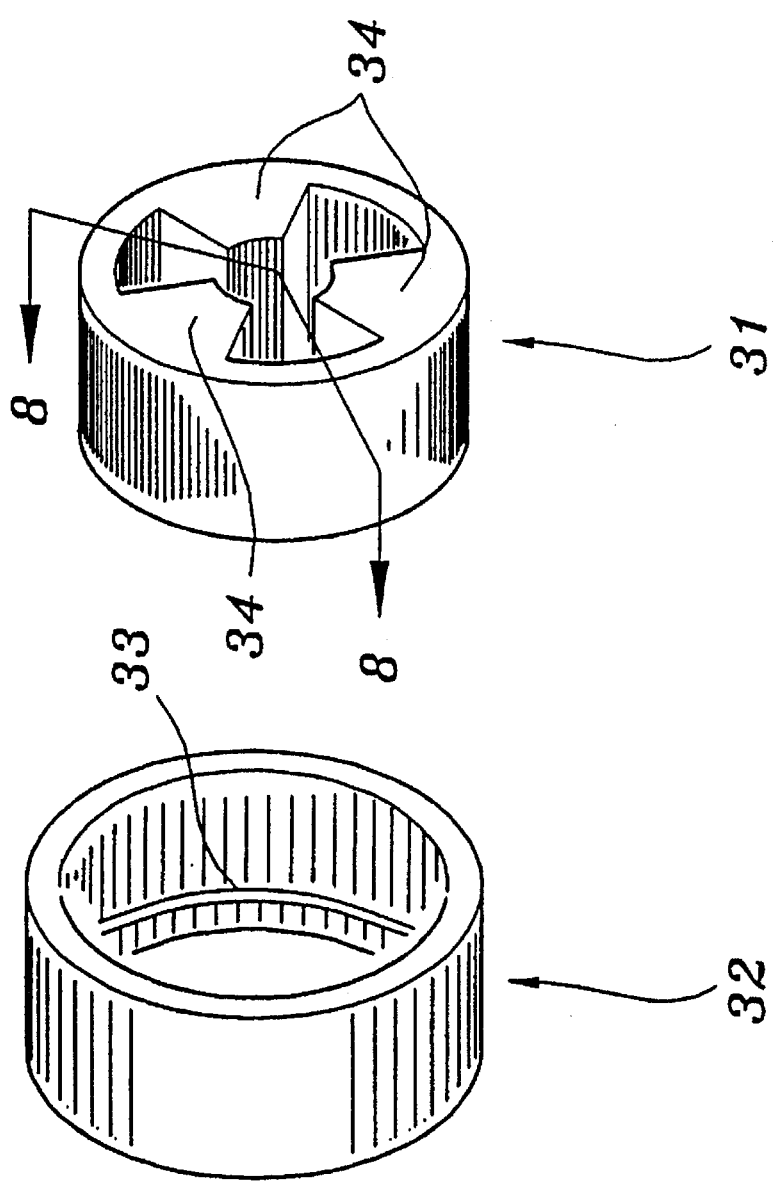
Fig. 7
Fig. 6

_ _ _

SHEATHED CATHETER ADAPTER AND METHOD OF USE

FIELD OF THE INVENTION

The present invention generally relates to an interface assembly for coupling two medical devices and more specifically to a novel catheter adapter, and related method, the adapter allowing the patient to breath directly through the adapter while also maintaining an enclosed environment around the catheter itself when the adapter is disconnected.

PRIOR ART

The relevant, known catheter adapter art falls into two categories. The first category comprises a closed system catheter which generally includes an adapter that leaves the catheter connected to the patient's ventilation system for a relatively long period of time during both use and non-use of the catheter. The interface formed by the adapter between the catheter assembly and the ventilation system is intentionally closed, thereby restricting the patient's access to oxygen to the respirator only. Such medical devices are tailored to long term health care needs where the patient requires frequent aspiration to clear the lungs of secretions through the ventilation system. U.S. Pat. No. 5,309,902 to Kee is typical of closed system catheter assemblies with an adapter made to be attached for long periods of time to a manifold.

Even though the closed system catheter assembly can be used a plurality of times before it is removed from the ventilation system, it nevertheless requires daily disconnection and replacement, thereby exposing medical personnel to possible contamination by the used catheter, unless a sterile environment is prepared by medical personnel beforehand. This type of adapter also intentionally lacks any means for direct atmospheric ventilation through the adapter. Further, there is no provision for effectively enclosing the withdrawn contaminated catheter within the adapter body in order to protect medical personnel against contamination.

The second category of catheter adapter comprises those used in single-use catheter devices for non-ventilated patients where the adapter forms an open interface with the endotracheal tube. U.S. Pat. No. 5,125,522 to Page et al, which is typical of this type of device, includes a sheathed catheter body which partially encapsulates the distal end of the catheter. Unfortunately, this type of "open" interface has serious deficiencies. The foremost deficiency is the risk to medical personnel of being exposed to contaminants during disconnection of the catheter adapter from the endotracheal tube due to the adapter's inability to properly contain the contaminants within the adapter body. To alleviate this risk, medical personnel are forced to take the time to prepare a sterile environment before withdrawing the catheter and disconnecting the adaptor for disposal. Secondly, medical personnel cannot be certain during use of such adapters that the airway through the adapter is completely clear of any obstructions and that the adaptor is allowing proper ventilation of the patient.

BRIEF SUMMARY AND OBJECT OF THE INVENTION

In brief summary, the preferred embodiment of the present invention overcomes and substantially alleviates the deficiencies in the prior art by providing a reliable, contamination free, distal end adapter for a suction catheter. The adapter allows the patient to breath directly therethrough when it is connected to the patient's endotracheal tube for use, and provides an enclosure for preventing exposure of medical personnel to contaminants when withdrawing the catheter from the patient and disconnecting the catheter adapter from the endotracheal tube for disposal.

Accordingly it is a dominant object of the present invention to provide a distal-end adapter for the catheter which provides enhanced sanitary protection from contaminated surfaces when the adapter is disconnected from a patient for disposal.

Another paramount object of the present invention is the provision of a distal-end adapter which provides easily viewable openings that allow the patient to directly breath through the adapter when in the connected position on the patient, and allow for simplified monitoring by medical personnel.

The above and other objects of the present invention are realized in a preferred embodiment thereof which includes a suction catheter distal-end adapter having prepositioned openings therein which align upon connection of the adapter to the patient's endotracheal tube to allow the patient to breath atmospheric air directly through the adapter when it is connected to the patient for use; and also provides an automatic closure member for substantially enclosing the withdrawn contaminated catheter therein when the adapter is disconnected from the endotracheal tube for disposal.

BRIEF DESCRIPTION OF THE DRAWINGS

FIG. 3 is an enlarged side view of the connector body;

FIG. 4 is a side view of the protective sleeve;

FIG. 5 is an end view of the protective sleeve showing the slitted flaps in a sealed position.

FIG. 6 is an enlarged side view of the sheath retainer;

FIG. 7 is an enlarged side view of the catheter guide.

FIG. 8 is an enlarged cross-section view of the catheter guide.

DETAILED DESCRIPTION OF THE ILLUSTRATED EMBODIMENT

Figure 1:
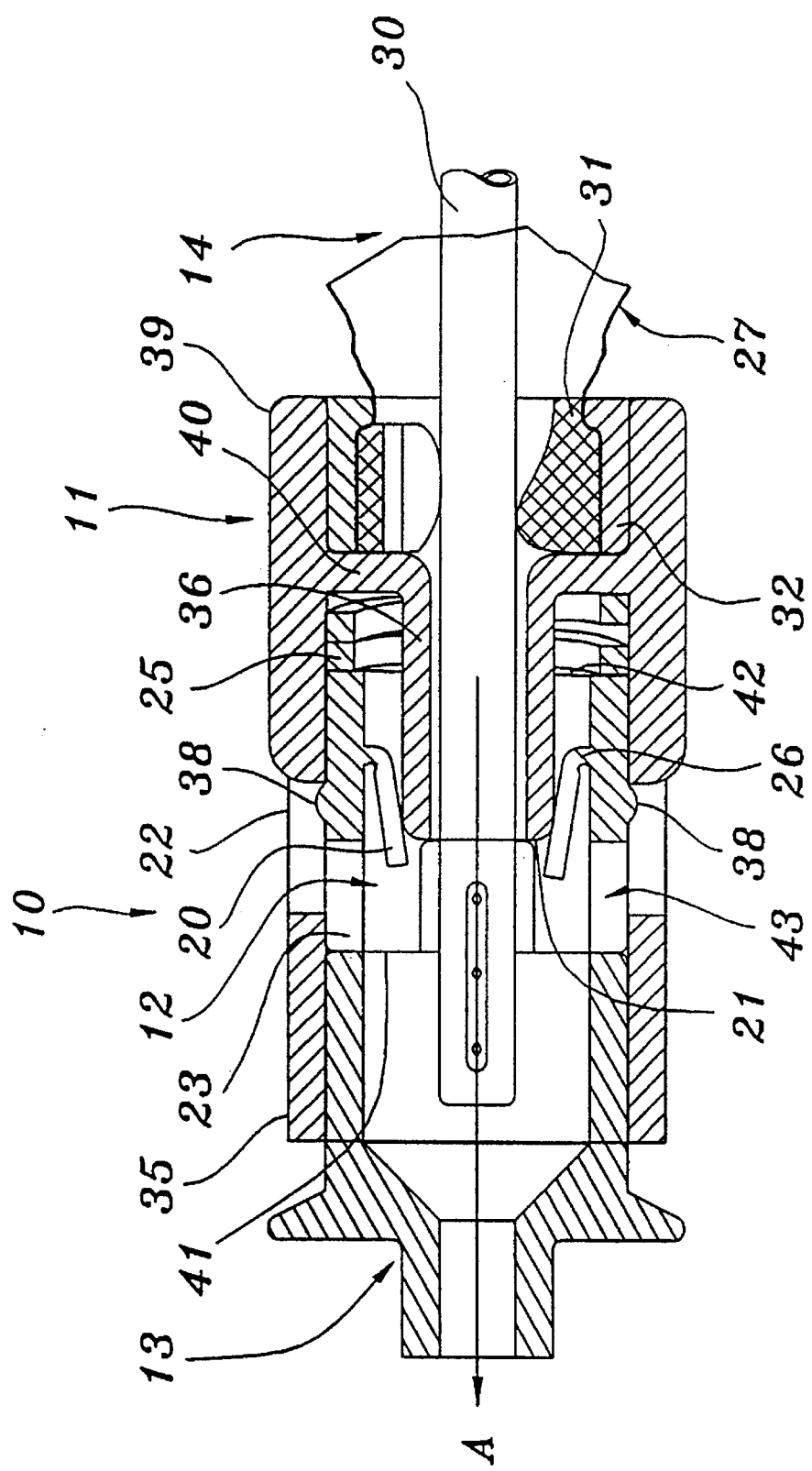
FIG.1 is a cross-sectional view of the distal-end adapter for an aspirating catheter illustrated in a connected position with respect to an endotracheal tube.

As shown in the exemplary drawings for the purposes of illustration, an embodiment of a distal-end adapter made in accordance with the principles of the present invention, referred to generally by the reference numeral 10, is provided for direct attachment to an endotracheal tube for use as an atmospheric ventilator and contaminant enclosure.

More specifically, as shown in FIG. 1, the distal-end adapter 10 is designed to be directly attached to an endotracheal tube assembly 13 in order to allow the aspiration of a patient's lungs of secretions using a sheathed catheter assembly 14 in conjunction with an aspirating device (not shown). The adapter 10 broadly comprises a connector body 11 and a protective sleeve 12 slidably disposed therein. The connector body 11 has a hollow tubular shape that allows for fluid flow communication therein. The connector body 11 also comprises a gripping portion 39 at its proximal end that extends to the midpoint of body 11. The gripping portion 39 further forms an annular abutting member 40 that extends inward from the gripping portion 39 and attaches to a tubular guide member 36 that extends toward and terminates at the midpoint of the connector body 11. At the midpoint, a plurality of air vents 22 are formed around the circumference of connector body 11.

FIG. 3 shows a perspective of the connector body 11 illustrating the plurality of air vents 22 around the midpoint area of the body 11. Also shown are gripping ridges 24 which act as a gripping surface for the user when disconnecting the endotracheal tube 13 from the adapter 10.

Referring back to FIG. 1, the protective sleeve 12 forms a tubular configuration with an open distal end 41 and a closed proximal end 42. The open distal end 41 of the protective sleeve 12 forms a plurality of slots 23 that extend around the circumference of end 41. At the closed proximal end 42, a spring 25 is attached thereto. FIG. 4 shows a perspective of the protective sleeve 12 that illustrates the spring 25 attached to the closed proximal end 42 of sleeve 12. Also shown are a plurality of stops 38 which are positioned directly behind each respective slot 23 of the protective sleeve 12. FIG. 5 is a cross-sectional view of the protective sleeve 12 shown in FIG. 4 along line 4—4 and illustrates the configuration of slots 23 and stops 38 around the circumference of sleeve 12 in relation to the flaps 20, which close off the lumen of the protective sleeve 12 and prevent fluid flow communication through the lumen when the protective sleeve 12 is in its disconnected position.

Figure 2:
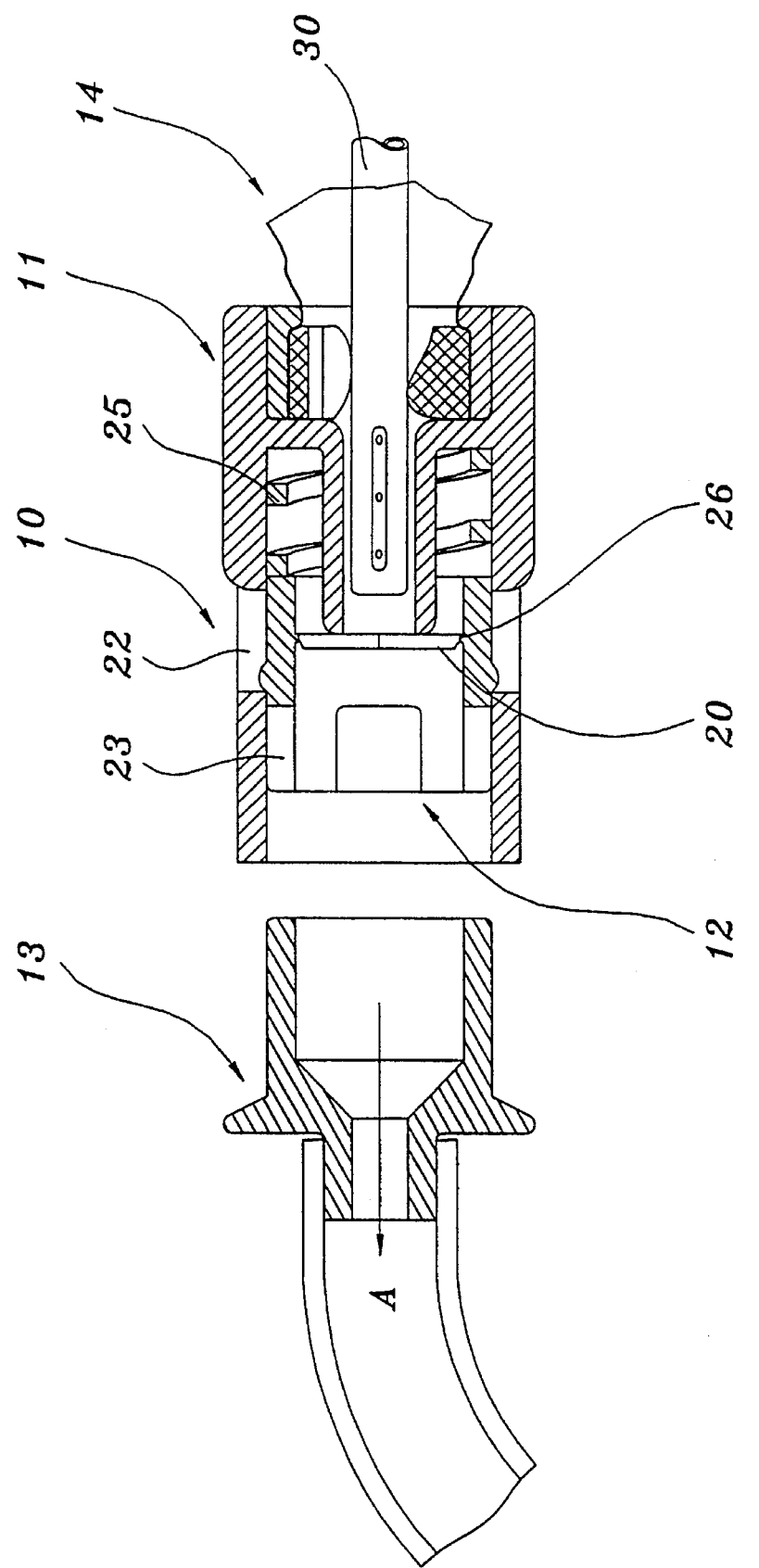
FIG. 2 is a cross-sectional view of the distal-end adapter illustrated in a disconnected position with respect to an endotracheal tube.

Referring now to both FIGS. 1 and 2, the interaction and operation of the protective sleeve 12 and the connector body 11 shall be explained. The protective sleeve 12 is allowed to slide within the connector body 11 whereby the adapter 10 has a connected position and a disconnected position with respect to the endotracheal tube 13. The protective sleeve 12 is positioned within the connector body 11 so as to be contacted and moved from a first, disconnected position to a second, connected position by the endotracheal tube 13 when the adapter 10 is attached thereto for use.

In the connected position, the connector body 11 is engaged with the protective sleeve 12 in such a manner that the flaps 20 covering the lumen of the protective sleeve 12 are pushed back by the endotracheal tube 13 at open distal end 41, thereby forcing the tubular guide member 36 of the connector body 11 against the distal end of the protective sleeve 12, and creating an opening 21 along axis A therethrough for a catheter 3e to pass into the endotracheal tube 13. Moreover, the engagement of the connector body 11 and the protective sleeve 12 align both the body 11 and the sleeve 12 so that any one air vent 22 is aligned with any one of the slots 23, thus forming an opening that allows the patient to breath atmospheric air directly through the formed opening 43.

Reference is now made to FIG. 2, which shows the adapter 10 disconnected from the endotracheal tube 13. In the disconnected position with the endotracheal tube 13, the connector body 11 disengages and the spring 25 forces the protective sleeve 12 to slide forward so that the flaps 20 are pushed back to their naturally closed position and forms an enclosure which effectively closes off the distal end of the adapter 10 when the catheter 3e is withdrawn and the adapter 10 is disconnected from the endotracheal tube 13. The hinges 26 are interposed between the proximal end of the flaps 20 and the interior surface of the protective sleeve 12 and operate to bias the flaps 20 to a closed position when the endotracheal tube 13 is disconnected from the adapter 10.

Referring now to FIGS. 1, and 6–8, the connector body 11 also holds in place the sheathed catheter assembly 14 at its proximal end. FIG. 1 demonstrates the catheter sheath 27 being held securely in place by attaching the catheter assembly 14 to the connector body 11. The distal end of the catheter assembly 14 connects to the proximal end of the connector body 11 and is interposed between retainer 32 and catheter guide 31. The retainer 32, shown in FIG. 6, is of an annular configuration and includes a ridge 33 located on the interior surface of the distal end of the retainer 32 which serves to lock the catheter assembly 14 in place during attachment of the assembly 14 to the connector body 11. The catheter guide 31 is disposed within the retainer 32 and serves to facilitate the entry of catheter 30 into the endotracheal tube 13.

FIG. 7 sets forth a perspective of the catheter guide 31 with a plurality of guide teeth 34 protruding inward from the interior surface of the guide 31 along its entire length. The guide teeth 34 have ridged shapes and are positioned in the catheter guide in such a manner that the teeth 34 are incongruent to one another and act together to facilely conduct the catheter 30 through the adapter 10 and into the endotracheal tube 13. Upon retraction of the catheter 30, the motion of catheter 30 through the incongruent configuration of teeth 34 generates a swirling action of the catheter tip along the airway. FIG. 8 illustrates a specific cross sectional view of the guide teeth 34 taken along line 8—8 of FIG. 7 showing their ridged configuration.

The connector body 11 and protective sleeve 12 as well as their constituent components may be made of any type of polymeric material. In the preferred embodiment, the connector body 11 is composed of a polyolefinic material and the protective sleeve 12 is made of nylon. Similarly, the retainer 26 may be made from nylon and the catheter guide 27 of a polyolefinic material.

Referring back to FIGS. 1, 2 and 3, the operation of the adapter 10 in the connected and disconnected positions will be explained in greater detail. In connecting the adapter 10 to the endotracheal tube 13 the user, handling the gripping ribs 24 of the connector body 11, slips the outer sleeve 35 of body 11 over the endotracheal tube 13 until the tube 13 engages the distal end of the protective sleeve 12 and begins to push the sleeve 12 backward. This backward action causes the flaps 20 of the protective sleeve 12 to be forced to an open position by the leading edge of tubular guide member 36 of the connector body 11. The backward motion of the protective sleeve 12 terminates when the stop 38 of sleeve 12 abuts against the gripping portion 39 of the connector body 11. In this position, the adapter 10 is fully engaged to the endotracheal tube 13.

Hinges 26 allow the flaps 20 to bend outward and create an opening when the tubular guide member 36 presses against flaps 20 by the backward motion of the protective sleeve 12 against the guide members 36.

In the connected position, FIG. I shows spring 25 of the protective sleeve 12 in a full, compressed state with the spring 25 being interposed between the annular abutting member 40 and the closed proximal end 42 of the sleeve 12.

The hinges 26 also bias the flaps 20 to a closed position when the adapter 10 is subsequently disconnected from the endotracheal tube 13 and the tubular guide members 36 no longer press the flaps 20 open by their presence.

FIG. 5 shows a front cross sectional view of flaps 20 in the closed position. The flaps 20 shown in FIG. 5 depict the preferred number of four flaps 20, although a plurality of three or more flaps 20 may be utilized in order to properly make and use the invention. When the endotracheal tube 13 is disconnected from the adapter 10, the spring 25 operates to bias the protective sleeve 12 forward, thereby releasing the flaps 20 into a closed position and effectively sealing off the distal end of the adapter 10 from leaking contaminants. In the preferred embodiment, the spring 25 is molded as an integral part of the protective sleeve 12, but may be made as a separate entity of any suitable type of polymeric material or metal.

As previously mentioned, the adapter 10 also allows the patient to breath atmospheric air directly through the adapter 10 body whenever the adapter 10 is connected to the endotracheal tube 13. In the connected position, the air vents 22 of the connector body 11 are aligned with the slots 23 of the protective sleeve 12. The air vent 22 and slot 23 combination form an opening 43 directly to the endotracheal tube 13 when the adapter 10 and tube 13 are fully engaged and allows the patient to breath directly through the adapter 10 body via the endotracheal tube 13. This opening 43 is also easily viewable by attending medical personnel to readily assure them that no air flow obstructions are present.

After the adapter 10 is fully engaged, medical personnel advance the catheter 30 through the catheter guide 31 and into the endotracheal tube 13 until the catheter 30 reaches the patient's lungs. Medical personnel then begin to aspirate the patient's lungs and airway until the lungs are sufficiently clear of unwanted secretions. Aspiration continues as medical personnel then withdraw the catheter 30 through the patient's airway until the catheter 30 is completely withdrawn into the adapter 10 body. During this withdrawal procedure, a swirling motion is imparted to the catheter 30 by the catheter guide 31 due to the incongruent configuration of the guide teeth 34. The swirling motion of the catheter 30 causes the catheter tip to pass near to a large area of the patient's tracheal wall as it is being withdrawn, thus improving aspiration of the patient's airway. When the adapter 10 and endotracheal tube 13 are disconnected, the protective sleeve 12 moves outward due to the bias of the spring 25, and the opening 43 closes due to the misalignment of the slots 23 and air vents 22. The sealing off of the opening 43 also serves to further encapsulate the distal end of the catheter 30 and prevent spillage of contaminants when the catheter 30 is withdrawn and the adapter 10 is disconnected from the endotracheal tube 13 for disposal.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

I claim:

1. An adapter for connecting a sheathed catheter to an endotracheal tube comprising:

a) a connector body having a distal end, a proximal end and a inner surface forming a lumen therethrough, said connector body further forming at least one opening therethrough which is in fluid flow communication with said connector body lumen; and b) a protective sleeve having a distal end, a proximal end, an exterior surface, and an inner surface forming a lumen therethrough, said protective sleeve being slidably disposed within said connector body lumen in a disconnected position, said protective sleeve further forming at least one opening therein and being slidable from said disconnected position in which said connector body opening is closed against fluid flow therethrough, to a connected position in which said protective sleeve opening is in fluid flow alignment with said connector body opening;

whereby, connection of said adapter to an endotracheal tube causes said protective sleeve to slide to said connected position.

2. The adapter according to claim 1, wherein said connector body is tubular, and said distal end and proximal end of said connector body are circular.

3. The adapter according to claim 1, wherein a plurality of gripping ribs extend from said connector body proximal end to a middle portion of said connector body, whereby said gripping ribs facilitate the connection and disconnection of said connector body to the endotracheal tube.

4. The adapter according to claim 1, wherein said protective sleeve openings and said connector body opening form an open air flow channel through said adapter when in said connected position, whereby a patient is allowed to breath atmospheric air directly through said adapter when said adapter is connected to the endotracheal tube placed in a patient's trachea.

5. An adapter for connecting a sheathed catheter to an endotracheal tube comprising:

a) a connector body having a distal end and a proximal end, and an inner surface forming a lumen therethrough; and b) a protective sleeve having a distal end, a proximal end, and an interior surface and forming a lumen therethrough, said protective sleeve being slidably disposed within said connector body lumen, said protective sleeve proximal end including a bias, said interior surface including slitted flaps positioned across said protective sleeve lumen;

whereby, attachment of said adapter to the endotracheal tube causes movement of said protective sleeve against said bias from a first, disconnected position in which said slitted flaps are closed against fluid flow through said protective sleeve lumen, to a second, connected position in which said slitted flaps are opened to fluid flow through said protective sleeve lumen.

6. The adapter according to claim 5, wherein said bias is a spring.

7. The adapter according to claim 6, wherein said spring is compressed in said connected position.

8. The adapter according to claim 6, wherein said spring is relaxed in said disconnected position.

9. The adapter according to claim 6, wherein said spring is a molded-in helical compression spring.

10. The adapter according to claim 5, wherein said bias is integrally formed with said protective sleeve.

11. An adapter for connecting a sheathed catheter to an endotracheal tube comprising:

a) a connector body having a distal end and a proximal end, forming a lumen therethrough, said connector body further forming at least an opening therethrough which is in fluid flow communication with said connector body lumen; and b) a protective sleeve having a distal end, a proximal end, an exterior surface and an interior surface and forming a lumen therethrough, said protective sleeve being slidably disposed within said connector body lumen in a disconnected position, said protective sleeve further forming at least one opening therein from the disconnected position in which said connector body opening is closed against fluid flow therethrough to a connected position in which said protective sleeve opening is in fluid flow alignment with said connector body opening, whereby connection of said adapter to an endotracheal tube causes said protective sleeve to slide toward said proximal end of said protective sleeve in relation with said connector body to a connected position in which said protective sleeve opening is in fluid flow alignment with said connector body opening, said interior surface including slitted flaps positioned across said protective sleeve lumen;

whereby, from a disconnected position said slitted flaps close off said lumen against fluid flow therethrough, to a connected position in which said slitted flaps open said protective sleeve lumen to fluid flow therethrough.

12. The adapter according to claim 11, wherein said connector body is tubular, and said distal end and proximal end of said connector body are circular.

13. The adapter according to claim 11, wherein a plurality of gripping ribs extend from said connector body proximal end to a middle portion of said connector body, whereby said gripping ribs facilitate the connection and disconnection of said connector body to the endotracheal tube.

14. The adapter according to claim 11, wherein said protective sleeve opening and said connector body opening form an open air flow channel through said adapter when in said connected position, whereby, a patient is allowed to breath atmospheric air directly through said adapter when said adapter is connected to the endotracheal tube placed in a patient's trachea.

15. A method of aspirating a patient's airway comprising the steps of:

a) providing an adapter having a connector body and a protective sleeve disposed within the connector body when the adapter is in the disconnected position, the protective sleeve forming a lumen therethrough;

b) connecting the adapter to an endotracheal tube;

c) inserting a catheter tube through the adapter and the endotracheal tube into a patient's airway;

d) aspirating the patient's airway of secretions using the catheter tube;

e) withdrawing the catheter tube from the patient's airway through the endotracheal tube and into the adapter;

f) disconnecting the adapter from the endotracheal tube and allowing said protective sleeve to close said lumen.

16. The method of aspirating a patient's airway according to claim 15, wherein said step of withdrawing said catheter causes a swirling motion of the catheter tip thereby allowing aspiration of a patient's tracheal wall as said catheter is withdrawn.

* * * * *